(12) United States Patent
Chappuis et al.

(10) Patent No.: US 6,814,734 B2
(45) Date of Patent: Nov. 9, 2004

(54) SURGICAL INSTRUMENTATION AND METHOD FOR FORMING A PASSAGE IN BONE HAVING AN ENLARGED CROSS-SECTIONAL PORTION

(75) Inventors: James L. Chappuis, Marietta, GA (US); Michael S. Veldman, Olive Branch, MS (US); Harold S. Taylor, Memphis, TN (US)

(73) Assignee: SDGI Holdings, Inc,, Wilmington, DE (US)

( * ) Notice: Subject to any disclaimer, the term of this patent is extended or adjusted under 35 U.S.C. 154(b) by 228 days.

(21) Appl. No.: 10/052,096

(22) Filed: Jan. 17, 2002

(65) Prior Publication Data

US 2002/0193799 A1 Dec. 19, 2002

Related U.S. Application Data

(60) Provisional application No. 60/298,985, filed on Jun. 18, 2001.

(51) Int. Cl.[7] ............................................... A61B 17/16
(52) U.S. Cl. ........................................ 606/80; 606/180
(53) Field of Search ................................. 606/80, 79, 84, 606/82, 167, 170, 176–180

(56) References Cited

U.S. PATENT DOCUMENTS

| | | | |
|---|---|---|---|
| 3,633,583 A | 1/1972 | Fishbein | |
| 3,702,611 A | 11/1972 | Fishbein | |
| 4,059,115 A | 11/1977 | Jumashev et al. | |
| 4,586,497 A | 5/1986 | Dapra et al. | |
| 4,646,738 A | 3/1987 | Trott | |
| 5,015,255 A | 5/1991 | Kuslich | |
| 5,062,845 A | 11/1991 | Kuslich et al. | |
| 5,306,284 A | * 4/1994 | Agee et al. | 606/170 |
| 5,431,671 A | 7/1995 | Nallakrishnan | |
| 5,445,639 A | 8/1995 | Kuslich et al. | |
| 5,549,679 A | 8/1996 | Kuslich | |
| 5,562,665 A | * 10/1996 | Young | 606/62 |
| 5,571,189 A | 11/1996 | Kuslich | |
| 5,591,170 A | * 1/1997 | Spievack et al. | 606/82 |
| 5,620,456 A | * 4/1997 | Sauer et al. | 606/185 |
| 5,928,239 A | 7/1999 | Mirza | |
| 5,954,722 A | 9/1999 | Bono | |
| 6,224,604 B1 | 5/2001 | Suddaby | |
| 6,383,188 B2 | * 5/2002 | Kuslich et al. | 606/80 |
| 6,440,138 B1 | * 8/2002 | Reiley et al. | 606/79 |
| 6,575,978 B2 | * 6/2003 | Peterson et al. | 606/83 |
| 6,679,886 B2 | * 1/2004 | Weikel et al. | 606/79 |
| 2001/0034526 A1 | 10/2001 | Kuslich et al. | |

* cited by examiner

*Primary Examiner*—David O. Reip
*Assistant Examiner*—Jessica R. Baxter
(74) *Attorney, Agent, or Firm*—Woodard, Emhardt, Moriarty, McNett & Henry LLP

(57) ABSTRACT

A surgical instrument and method for forming a passage in bone having an enlarged cross-sectional portion is provided. The instrument includes an elongate member and a cutting element engaged thereto and transitionable between a retracted configuration for extending through a first portion of the passage and an expanded configuration for forming a second portion of the passage having an enlarged cross-section. In one embodiment, the cutting element is transitioned between the retracted and expanded configurations by axially displacing the cutting element relative to the elongate member. In another embodiment, the elongate member includes a tapping thread configured to cut threads along the first portion of the passage, and the cutting element is a blade configured to form the enlarged cross-section when transitioned to the expanded configuration. In another embodiment, the cutting element is arranged in an axial orientation when in the retracted configuration and an angular orientation when in the expanded configuration.

38 Claims, 11 Drawing Sheets

SURGICAL INSTRUMENTATION AND METHOD FOR FORMING A PASSAGE IN BONE HAVING AN ENLARGED CROSS-SECTIONAL PORTION

CROSS REFERENCE TO RELATED APPLICATIONS

The present application claims the benefit of Provisional Application Ser. No. 60/298,985, filed on Jun. 18, 2001 and entitled Variable Diameter Passage Tap Apparatus, the contents of which are hereby incorporated by reference in their entirety.

FIELD OF THE INVENTION

The present invention relates generally to the field of surgical instrumentation and methods, and more specifically relates to surgical instrumentation and methods for forming a passage in bone having an enlarged cross-sectional portion, and more particularly within a vertebral body.

BACKGROUND OF THE INVENTION

Skeletal members are formed of bone tissue and other structures such as cartilage. For various reasons, skeletal members sometimes fracture, weaken or deteriorate over time. In other instances, skeletal members may be deformed or diseased. In either case, treatment of the skeletal member usually requires some type of artificial support or stabilization to promote healing and/or correction of abnormalities.

With specific regard to treatment of the spine, plates or rods are typically attached to the portion of the spinal column being treated to provide the requisite amount of support and/or stabilization. In many cases, attachment of the plates or rods to the spine is accomplished by engaging a number of bone anchors, such as bone screws, to one or more vertebral bodies. In such applications, the bone screws are sometimes engaged to the vertebral bodies via extension through the pedicle which is mostly comprised of cancellous or porous bone tissue. When dealing with patients having soft bone tissue or with patients afflicted with a bone weakening disease (e.g., osteoporosis), conventional bone screws have a tendency to cut out or loosen as a result of insufficient bone strength.

To compensate for soft or weakened bone tissue, bone cement or another type of material is sometimes introduced adjacent the threaded portion of the bone screw to strengthen the bone. The bone cement provides a more secure anchoring arrangement to prevent the screw from cutting out or loosening. The cement material is typically introduced into the bone via passage through an axial opening extending along a length of the screw and exiting through a series of fenestration openings in communication with the axial opening and positioned at intermittent location along the length of the screw. Preferably, the bone cement should be distributed uniformly about the threaded portion of the bone screw with minimal disruption to the adjacent bone tissue.

In a prior method for treating the spine using bone screws, a uniform passage having a diameter equal to or slightly less than the screw diameter is formed through the pedicle region of the vertebral body. A bone screw is then threaded into the passage to a predetermined insertion depth, with the threads of the bone screw engaged tightly against adjacent bone tissue. Once the bone screw is properly positioned within the vertebral body, bone cement is injected through the axial opening in the bone screw and introduced into the bone by way of a number of the fenestration openings. Notably, this method of screw insertion and anchoring typically results in an uneven distribution of bone cement around the threaded portion of the bone screw. Additionally, rapid injection of the bone cement can lead to fluid pressure buildup, sometimes resulting in disruption of the cancellous bone tissue in the area adjacent the fenestration openings.

In another prior method for treating the spine using bone screws, a uniform passage having a diameter somewhat larger than the screw diameter is formed through the pedicle region of the vertebral body. In a specific application, the diameter of the passage is about 1.5 to 2.0 millimeters larger than the diameter of the bone screw. The bone screw is then inserted into the passage, and once properly positioned within the vertebral body, bone cement is introduced into the passage to fill up the void or spacing between the screw and the walls of the passage. However, this method of screw insertion and anchoring requires the formation of an oversized screw insertion passage extending through the pedicle. Notably, the formation of an oversized passage results in the removal of a relatively large amount of vertebral bone tissue, thereby tending to compromise the structural integrity of the pedicle.

Thus, there is a general need in the industry to provide improved surgical instrumentation and methods for forming a passage in bone having an enlarged cross-sectional portion than is currently available within the industry. The present invention meets this need and provides other benefits and advantages in a novel and unobvious manner.

SUMMARY OF THE INVENTION

The present invention relates generally to surgical instrumentation and methods for forming a passage in bone having an enlarged cross-sectional portion. While the actual nature of the invention covered herein can only be determined with reference to the claims appended hereto, certain forms of the invention that are characteristic of the preferred embodiments disclosed herein are described briefly as follows.

In one form of the present invention, a surgical instrument is provided which includes an elongate member and at least one cutting element engaged thereto. The cutting element is transitionable between a retracted configuration capable of extending through a first portion of a passage in bone and an expanded configuration capable of forming a second portion of the passage having an enlarged cross-section, with axial displacement of the cutting element relative to the elongate member causing the cutting element to transition between the retracted and expanded configurations.

In another form of the present invention, a surgical instrument is provided which includes an elongate member, a first cutting element disposed along the elongate member for forming a first portion of a passage in bone, and a second cutting element disposed along the elongate member and being transitionable between a retracted configuration for extending through the first portion of the passage and an expanded configuration for forming a second portion of the passage having an enlarged cross-sectional portion.

In another form of the present invention, a surgical instrument is provided which includes an elongate member, a tapping thread defined along at least a portion of the elongate member configured to form a threaded portion of a passage in bone, and a cutting element engaged with the elongate member and being transitionable between a retracted configuration for extending through the threaded portion of the passage and an expanded configuration for forming an enlarged cross-sectional portion of the passage.

In another form of the present invention, a surgical instrument is provided which includes means for tapping threads along a portion of a passage in bone, means for forming an enlarged cross-sectional portion of the passage, and means for transitioning the means for forming between a retracted configuration for extending through the threaded portion of the passage and an expanded configuration for forming the enlarged cross-sectional portion of the passage.

In another form of the present invention, a surgical instrument is provided which includes an elongate member extending along an axis and including an expandable portion having at least one cutting element that is transitionable between an axial orientation for forming an axial passage in bone and an angular orientation for enlarging a portion of the axial passage.

In another form of the present invention, a surgical instrument is provided which includes an elongate member and at least one cutting element engaged with the elongate member and being transitionable between a retracted configuration for extending through a passage in bone and an expanded configuration for enlarging a portion of the passage, with the cutting element being outwardly biased toward the expanded configuration. The instrument also includes a retention element interacting with the cutting element to selectively maintain the cutting element in the retracted configuration.

In another form of the present invention, a surgical method is provided which includes the steps of providing a surgical instrument having an elongate member and at least one cutting element engaged with the elongate member and being transitionable between a retracted configuration and an expanded configuration, forming a passage in bone, displacing the cutting element along the passage while in the retracted configuration, transitioning the cutting element to the expanded configuration and enlarging a portion of the passage, transitioning the cutting element to the retracted configuration and removing the surgical instrument from the passage.

It is one object of the present invention to provide improved surgical instrumentation and methods for forming a passage in bone tissue having an enlarged cross-section portion.

Further objects, features, advantages, benefits, and aspects of the present invention will become apparent from the drawings and description contained herein.

DESCRIPTION OF THE ILLUSTRATED EMBODIMENTS

Figure 1:
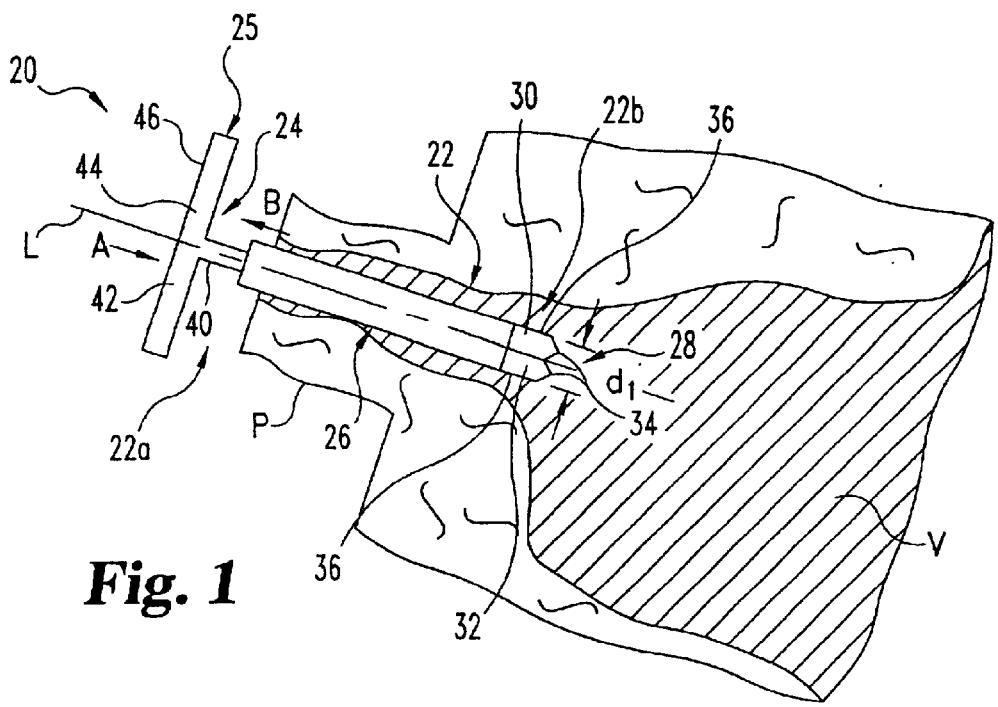
FIG. 1 is a partial cross-sectional side view of a skeletal member illustrating a surgical instrument according to one form of the present invention, as shown in a closed-tip configuration.

For the purposes of promoting an understanding of the principles of the invention, reference will now be made to the embodiments illustrated in the drawings and specific language will be used to describe the same. It will nevertheless be understood that no limitation on the scope of the invention is hereby intended, and that alterations and further modifications in the illustrated devices and further applications of the principles of the invention as illustrated herein are contemplated as would normally occur to one skilled in the art to which the invention relates.

Figure 2:
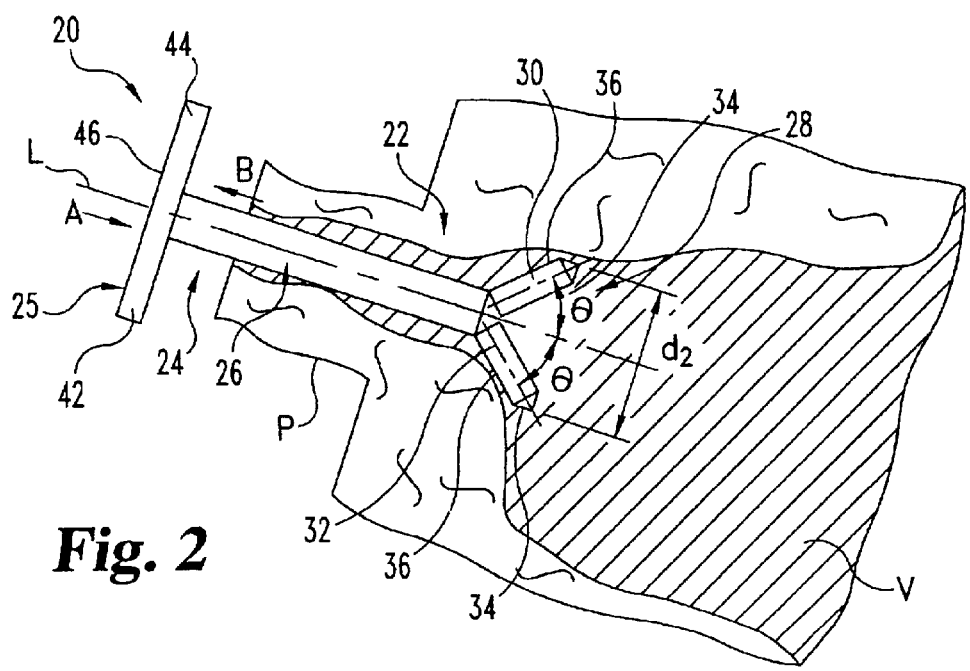
FIG. 2 is the surgical instrument illustrated in FIG. 1, as shown in an open-tip configuration.

Referring to FIGS. 1 and 2, shown therein is a surgical instrument 20 according to one form of the present invention. As will be discussed in detail below, the instrument 20 and other embodiments of the present invention are used to form a passage in a skeletal member having an enlarged cross-sectional portion. In one embodiment of the invention, the surgical instruments and methods illustrated and described herein are used in association with treatment of the spine. It should be understood, however, that the present invention may also be used in association with applications outside of the spinal field. It should also be understood that although the present invention is illustrated and described in the context of treatment of a human spine, the treatment of other animals is also contemplated. Moreover, although the present invention is illustrated and described as being used in association with intrabody applications to form a passage in a vertebral body for receiving a bone anchor, it should be understood that other applications are also contemplated. For example, the present invention could also be used in association with interbody applications to form a passage between adjacent vertebral bodies, with the passage having an enlarged cross-sectional portion sized to receive a spinal implant such as a threaded or unthreaded fusion cage.

The surgical instrument 20 is generally comprised of an elongate member 22 and an actuator mechanism 24. The elongate member 22 extends generally along a longitudinal axis L and has a proximal end portion 22a and a distal end portion 22b. The actuator mechanism 24 includes an actuator handle 25 disposed adjacent the proximal end portion 22a of the elongate member 22. Although the illustrated embodiment depicts the elongate member 22 as having a generally linear configuration, it should be understood that other configurations are also contemplated, such as, for example, a curvilinear configuration or an angled configuration.

The elongate member 22 is generally comprised of a hollow shaft or sleeve 26 and an expandable tip 28 extending from the distal end portion of the sleeve 26. The expandable tip 28 includes a pair of cutting elements 30, 32 that are transitionable between a retracted or closed configuration (FIG. 1) for forming an axial passage in the vertebral body V, and an expanded or open configuration (FIG. 2) for forming an enlarged cross-sectional portion of the axial passage. When in the retracted configuration, the cutting elements 30, 32 are preferably aligned generally along longitudinal axis L and preferably have an outer cross-section equal to or less than the outer cross-section of the sleeve 26. When in the expanded configuration, the cutting elements 30, 32 are preferably angled relative to longitudinal axis L at an acute angle θ and define an enlarged outer cross-section relative to the retracted configuration. In one embodiment of the invention, when in the angular orientation, the cutting elements 30, 32 are angled at an angle θ of about 45 degrees. However, it should be understood that other angles are also contemplated as falling within the scope of the present invention, including any angle θ falling between 0 degrees and 180 degrees. As will be discussed in greater detail below, the expandable tip 28 is configured to transition between the axial and angular orientations in response to a mechanically induced force. Such force may be effected, for example, via the selective actuation of the actuator mechanism 24.

Although the expandable tip 28 has been illustrated and described as including a pair of cutting elements 30, 32 disposed generally opposite one another, it should be understood that the tip 28 could be comprised of any number of cutting elements, including a single cutting element or three or more cutting elements. Additionally, although the cutting elements 30, 32 have been illustrated and described as being positioned adjacent the distal end 22b of the elongate member 22, it should be understood that the cutting elements 30, 32 may be disposed at other axial locations as well. It should also be understood that a series of cutting elements may be disposed at multiple axial locations along the elongate member 22.

The cutting elements 30, 32 preferably have distal ends 34 that are pointed to facilitate penetration into bone tissue to form an axial passage in the vertebral body V when the cutting elements 30, 32 are disposed in the axial orientation. However, it should be understood that other configurations of the distal ends 34 are also contemplated. For example, the distal ends 34 could alternatively have a blunt configuration, such as a rounded or flat shape, or could have any other suitable shape or configuration as would occur to one of skill in the art. The cutting elements 30, 32 also preferably include at least one cutting edge 36 to facilitate formation of the axial passage when disposed in the axial orientation, and to facilitate formation of an enlarged cross-sectional portion after the cutting elements 30, 32 are transitioned to the angular orientation. In one embodiment of the invention, the cutting edge 36 is defined by a cutting blade extending generally along the longitudinal axis L. In another embodiment of the invention, the cutting edge 36 is defined by a flute, such as, for example, an axial or helical drill flute. In yet another embodiment of the invention, the cutting edge 36 is defined by a tapping thread configured to form threads along the inner wall of the axial passage. In still another embodiment of the invention, a cutting edge may be formed along a portion of the sleeve 26 to facilitate formation of the axial passage in the vertebral body V.

Figure 3:
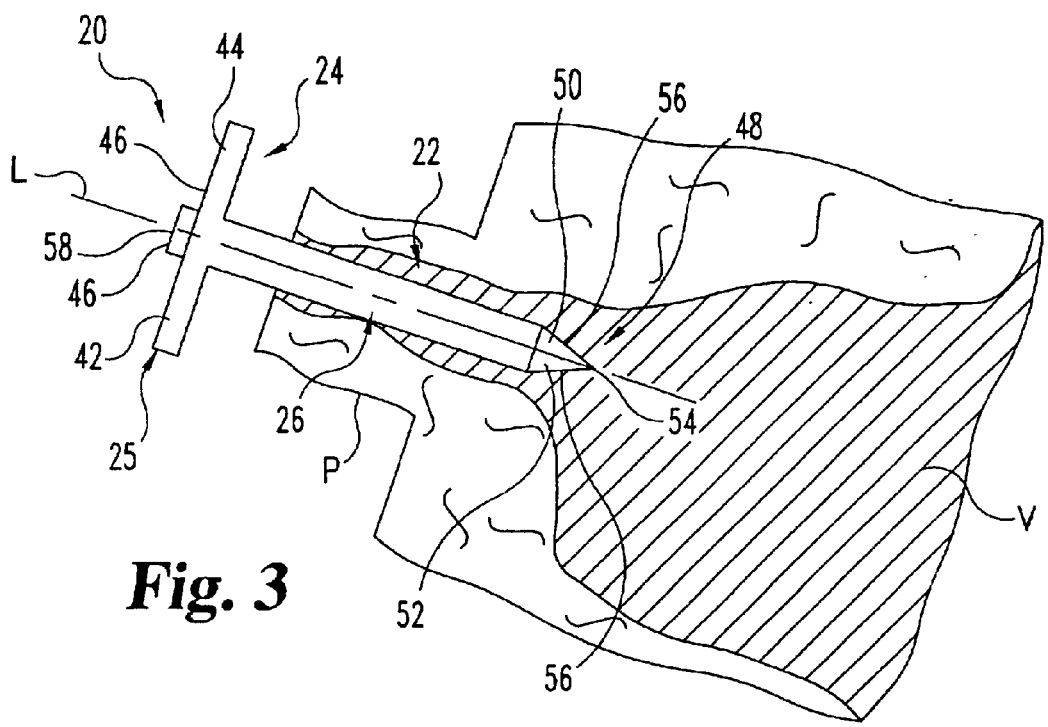
FIG. 3 is a partial cross-sectional side view of a skeletal member illustrating a surgical instrument according to another embodiment of the present invention, as shown in a closed-tip configuration.

Although one specific embodiment of the cutting elements 30, 32 has been illustrated and described herein, it should be understood that other shapes and configurations of cutting elements are also contemplated. Indeed, any cutting element that is suitable for cutting bone tissue to form a passage having an enlarged cross-sectional portion is contemplated as falling within the scope of the present invention. For example, as shown in FIG. 3, the expandable tip 48 includes a pair of opposing cutting elements 50, 52. The distal end portions of the cutting elements 50, 52 are inwardly tapered so as to define a streamlined, wedge-shape or conical configuration when the cutting elements 50, 52 are disposed in an axial orientation. Notably, the cutting elements 50, 52 define a single pointed tip 54 when disposed in the axial orientation, thereby tending to further aid in the formation of the axial passage in the vertebral body V. Similar to cutting elements 30, 32, the cutting elements 50, 52 preferably include at least one cutting edge 56 to facilitate formation of the axial passage and the enlarged cross-sectional portion of the passage after the cutting elements 50, 52 are transitioned to an angular orientation. Aside from the shape and configuration of the cutting elements 50, 52, the expandable tip 48 functions in a manner similar to that of the expandable tip 28.

In a preferred embodiment of the invention, the cutting elements 30, 32 are biased or urged away from one another toward the angular orientation illustrated in FIG. 2. The biasing force may be generated by one or more biasing mechanisms (not shown), such as, for example, a spring or spring-like device. The cutting elements 30, 32 are preferably selectively maintained in the axial orientation illustrated in FIG. 1 by a retention mechanism. In one embodiment of the invention, the sleeve 26 functions as the retention mechanism. As illustrated in FIG. 1, at least a portion of each cutting element 30, 32 is initially disposed within the sleeve 26 to prevent the cutting elements 30, 32 from opening or expanding toward the angular orientation. However, as illustrated in FIG. 2, when the expandable tip 28 is axially displaced relative to the sleeve 26 such that the cutting elements 30, 32 are displaced beyond the distal end of sleeve 26, the cutting elements 30, 32 are transitioned or expanded toward the angular orientation.

In one embodiment of the invention, the actuator mechanism 24 is generally comprised of an actuator handle 25 and a drive shaft 40. The actuator handle 25 includes a pair of arms 42, 44 extending laterally from a proximal end portion of the drive shaft 40 in generally opposite directions. The drive shaft 40 is preferably slidably and rotatably disposed within the sleeve 26, with the cutting elements 30, 32 being operatively coupled to the distal end portion of shaft 40. In one embodiment of the invention, the cutting elements 30, 32 are pivotally coupled to the distal end portion of shaft 40. However, it should be understood that other suitable means for coupling the cutting elements 30, 32 to the distal end portion of shaft 40 are also contemplated as falling within the scope of the present invention.

Figure 4:
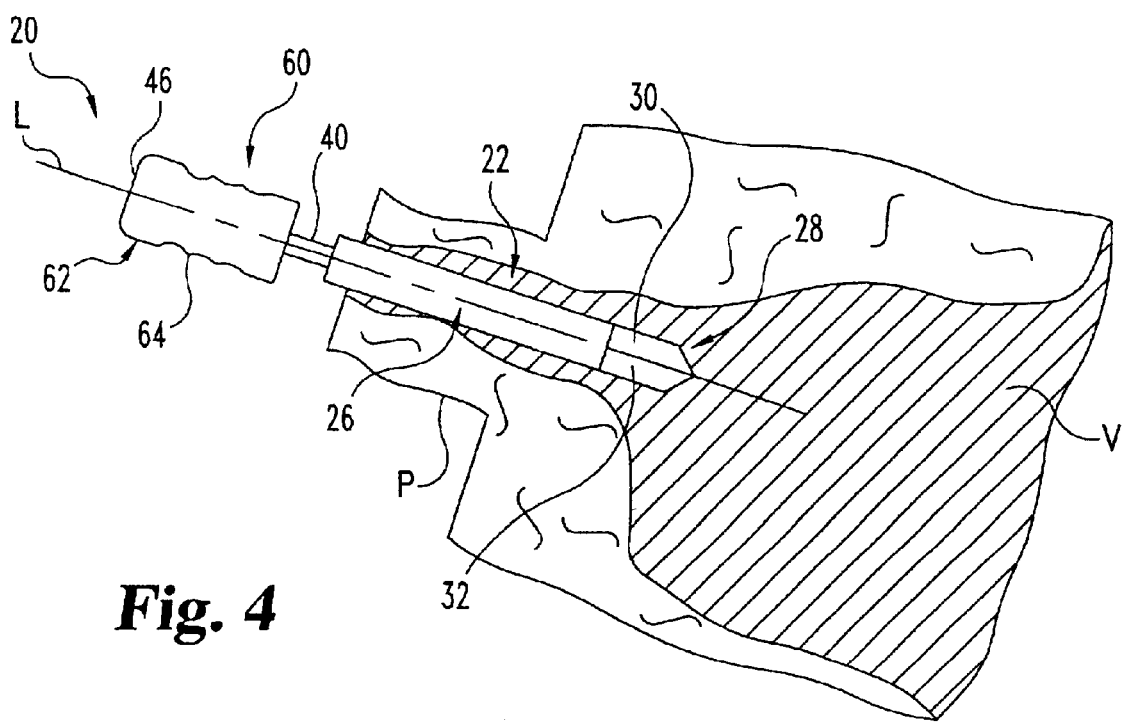
FIG. 4 is a partial cross-sectional side view of a skeletal member illustrating a surgical instrument according to another embodiment of the present invention, as shown in a closed-tip configuration.

The arms 42, 44 of the actuator handle 25 preferably extend perpendicularly from the drive shaft 40 to form a T-handle arrangement. However, other shapes and configurations of actuator handle 25 are also contemplated. For example, as shown in FIG. 3, instead of being connected to drive shaft 40, the arms 42, 44 of actuator handle 25 may alternatively be connected to and extend laterally from the sleeve 26. As also shown in the embodiment of FIG. 3, an actuator knob 58 may be operatively attached to the proximal end portion of the drive shaft 40. In another embodiment of the invention illustrated in FIG. 4, the T-shaped actuator handle 25 may be replaced by an actuator handle 60 extending generally along longitudinal axis L. The actuator handle 60 is operatively attached to the proximal end portion of the drive shaft 40 and includes a cylindrical-shaped gripping portion 62 defining a contoured gripping surface 64. Aside from its shape and configuration, the actuator handle 60 functions in a manner similar to that of actuator handle 25.

The actuator handle 25, 60 preferably defines an axially facing bearing or tapping surface 46 configured to provide a means for applying an axial force to the drive shaft 40 and/or the sleeve 26 to facilitate formation of the axial passage within the vertebral body V. The bearing surface 46 may be defined by the arms 42, 44, the cylindrical gripping portion 62, the proximal end of sleeve 26, and/or the actuator knob 58. Preferably, the bearing surface 46 is generally flat such that an axial force might be applied directly by the user's hand and/or by way of a driving tool, such as, for example, a mallet or another type of impact tool.

Application of an axial force to the bearing surface 46 correspondingly transmits an axial force to the drive shaft 40, and more specifically to the cutting elements 30, 32. As should be apparent, application of an axial force to the actuator handle 24, 60 when the cutting elements 30, 32 are in an axial orientation will cause the cutting elements 30, 32 to penetrate and cut into bone tissue to form an axial passage in the vertebral body V. Although the distal ends 34 of the cutting elements 30, 32 are illustrated and described as extending beyond the distal end of the sleeve 26 when in the axial orientation, it should be understood that the distal ends 34 could alternatively be disposed entirely with the sleeve 26 when disposed in the axial orientation. In such an embodiment, the sleeve 26 may be configured to form the axial passage within the vertebral body V. For example, the distal end of sleeve 26 could be configured to include a cutting edge to facilitate penetration and cutting into bone tissue. Alternatively, an axial passage could be preformed into the vertebral body V via a separate instrument, such as, for example, a conventional drill or reamer, with the instrument 20 being used to form an enlarged portion of the pre-formed passage.

Following formation of the axial passage in the vertebral body V, the expandable tip 28 is transitioned from the axial orientation illustrated in FIG. 1 toward the angular orientation illustrated in FIG. 2. As discussed above, such transitioning may occur in response to the application of a mechanically induced force, such as might be effected, for example, by displacing the actuator handle 25 relative to the sleeve 26. In one embodiment of the invention, axial displacement of the drive shaft 40 relative to the sleeve 26 correspondingly causes the cutting elements 30, 32 to transition between the axial and angular orientations. Such axial displacement may be effected by applying an axial force to the actuator handle 25 while maintaining the sleeve 26 in a stationary position, or by pulling the sleeve 26 toward the arms 40, 42 of actuator handle 25 while maintaining the handle 25 in a stationary position, or by a combination of these operations. In an alternative embodiment of the invention, the surgical instrument 20 could be configured such that rotational displacement of the sleeve 26 relative to the drive shaft 40 would correspondingly cause relative axial displacement between the sleeve 26 and the expandable tip 28. Such an operation might be accomplished, for example, by providing the drive shaft 40 with external threads which engage internal threads defined along the interior of sleeve 26. As should be apparent, rotating the handle 25 about the longitudinal axis L would correspondingly axially displace the drive shaft 40 and the expandable tip 28 relative to the sleeve 26 to transition the cutting elements 30, 32 between the axial and angular orientation.

Once the expandable tip 28 is transitioned to the angular orientation illustrated in FIG. 2, a rotational force (i.e., torque) is applied to the actuator handle 25. Rotating the actuator handle 25 in turn rotates the cutting elements 30, 32 generally about the longitudinal axis L to facilitate enlargement of a cross-sectional portion of the axial passage in the vertebral body V. The rotational force or torque may be applied directly by the user's hand via the arms 42, 44 of handle 25, or by a driving tool such as a wrench or drive motor. The rotational force or torque exerted onto the handle 25 is in turn transmitted to the cutting elements 30, 32, either directly via the drive shaft 40 or indirectly via the sleeve 26. As should be apparent, rotating the cutting elements 30, 32 about the longitudinal axis L when the cutting elements 30, 32 are in the angular orientation illustrated in FIG. 2 will cause the cutting edges 36 to cut into the bone tissue to enlarge the distal end portion of the axial passage in the vertebral body V.

Having described the various structural features of the surgical instrument 20, a method of using the surgical instrument 20 will now be discussed in accordance with one form of the present invention. Referring once again to FIG. 1, when the expandable tip 28 is disposed in the axial or retracted orientation, the cutting elements 30, 32 are generally aligned with the longitudinal axis L and define an outer diameter $d_1$ that is preferably equal to or slightly less than the outer diameter of the sleeve 26. An axial force is applied to the actuator handle 25 in the direction of arrow A, which in turn causes the cutting elements 30, 32 to penetrate and cut into bone tissue to form an axial passage through the pedicle P and into the vertebral body V. The axial passage preferably has an inner diameter substantially equal to the outer diameter $d_1$ of the expandable tip 28. As described above, such axial force may be applied to the axially facing surface 46, either directly by the user's hand or by way of an impact tool. In another embodiment of the invention, a rotational force may be applied to the handle 25 to rotate the cutting elements 30, 32 about the longitudinal axis L to cause the cutting edges 36 and the distal tips 34 to cut into bone tissue to form the axial passage in the vertebral body V. In yet another embodiment, both an axial and rotational force may be applied to the handle 25 to form the axial passage in the vertebral body V.

Although the axial passage extending through the pedicle P and the vertebral body V has been illustrated and described as having a generally circular cross-section, other cross sections are also contemplated as falling within the scope of the present invention. For example, the axial passage may have an elliptical, rectangular, or polygonal cross-section, or any other suitable cross-section that would be apparent to one of skill in the art. Moreover, although the surgical instrument 20 has been illustrated and described as being used to form the axial passage, it should be understood that an axial passage having a diameter $d_1$ may be preformed in the vertebral body V. In such case, the expandable tip 28 may be displaced along the preformed axial passage (while in the axial orientation) until disposed in the position illustrated in FIG. 1.

Following formation of the axial passage, the cutting elements 30, 32 are transitioned toward the angular or expanded orientation illustrated in FIG. 2 to form an enlarged cross-sectional portion of the passage. As discussed above, such transitioning may be accomplished by displacing the expandable tip 28 relative to the sleeve 26, either by displacing the handle 25 and drive shaft 40 in the direction of arrow A and/or by displacing the sleeve 26 in the direction of arrow B. When transitioned to the angular orientation, the cutting elements 30, 32 are each disposed at an angle θ relative to the longitudinal axis L to define an enlarged/expanded outer cross-section.

After being transitioned to the angular orientation, the cutting elements 30, 32 are rotated about the longitudinal axis L which causes the cutting edges 36 and the distal tips 34 to cut into vertebral bone tissue to form an enlarged cross-sectional portion of the axial passage having a diameter $d_2$. In an alternative embodiment of the invention, an axial force may be applied to handle 25 in the direction of arrow A to cause the cutting elements 30, 32 to penetrate and cut into vertebral bone tissue to form the enlarged cross-sectional portion of the axial passage. In another embodiment, both a rotational force and an axial force may be applied to the handle 25 to form the enlarged cross-sectional portion of the axial passage. It should be understood that the cutting elements 30, 32 need not necessarily be instantaneously transitioned to the angular orientation illustrated in FIG. 2, but may be gradually transitioned toward the angular orientation during formation of the enlarged cross-sectional portion of the axial passage. Furthermore, although the enlarged portion of the axial passage has been illustrated and described as having a generally circular cross-section, as discussed above, other cross-sections are also contemplated as falling within the scope of the present invention.

Following formation of the enlarged cross-sectional portion of the axial passage, the cutting elements 30, 32 are transitioned back to the axial orientation illustrated in FIG. 1 and the expandable tip 28 and the remainder of the instrument 20 are removed from the vertebral body V. A bone anchor (not shown) may then be inserted into the axial passage, preferably having an outer diameter closely corresponding to the inner diameter $d_1$ of the axial passage. The enlarged portion of the axial passage is then filled with an anchoring material, such as bone cement or other known anchoring material, to secure the bone anchor in position. In one embodiment of the invention, the bone anchor may be configured as a fenestrated bone screw defining an axial opening extending at least partially therethrough and a series of fenestration openings disposed in communication with the axial opening. One embodiment of a fenestrated bone screw suitable for use in association with the present invention is described in U.S. patent application Ser. No. 09/746,668 to Chappuis, filed on Dec. 20, 2000, the contents of which are hereby incorporated by reference. It should be understood, however, that other suitable bone anchors are also contemplated for use with the present invention, including both threaded and unthreaded bone anchor devices.

The bone screw is preferably positioned within the vertebral body V with the fenestration openings disposed adjacent the enlarged cross-sectional portion of the axial passage. As a result, bone cement may be injected through the axial opening in the bone screw, out the fenestration openings, and into the enlarged cross-sectional portion of the axial passage. As should be appreciated, the enlarged cross-sectional portion of the axial passage facilitates uniform distribution of the bone cement around the threaded portion of the bone screw while minimizing disruption to the cancellous bone tissue surrounding the bone screw.

Once the bone cement cures or hardens, a cement mantle is formed about a portion of the bone screw to more firmly secure the bone screw within the vertebral body V. As should be appreciated, the cement mantle eliminates or at least minimizes the likelihood of the bone screw from loosening or cutting away from the vertebral body V. As should also be appreciated, enlargement of only a portion of the axial passage to the enlarged diameter $d_2$, while maintaining the remainder of the axial passage at the diameter $d_1$, reduces the amount of bone material removed from the vertebral body V. As a result, disruption of the structural integrity of the vertebral body V, and particularly the pedicle P, is likewise minimized. In this manner, formation of the axial passage in the vertebral body V and securing the bone screw within the axial passage by way of a cement mantle is accomplished in a minimally invasive manner.

Figure 5:
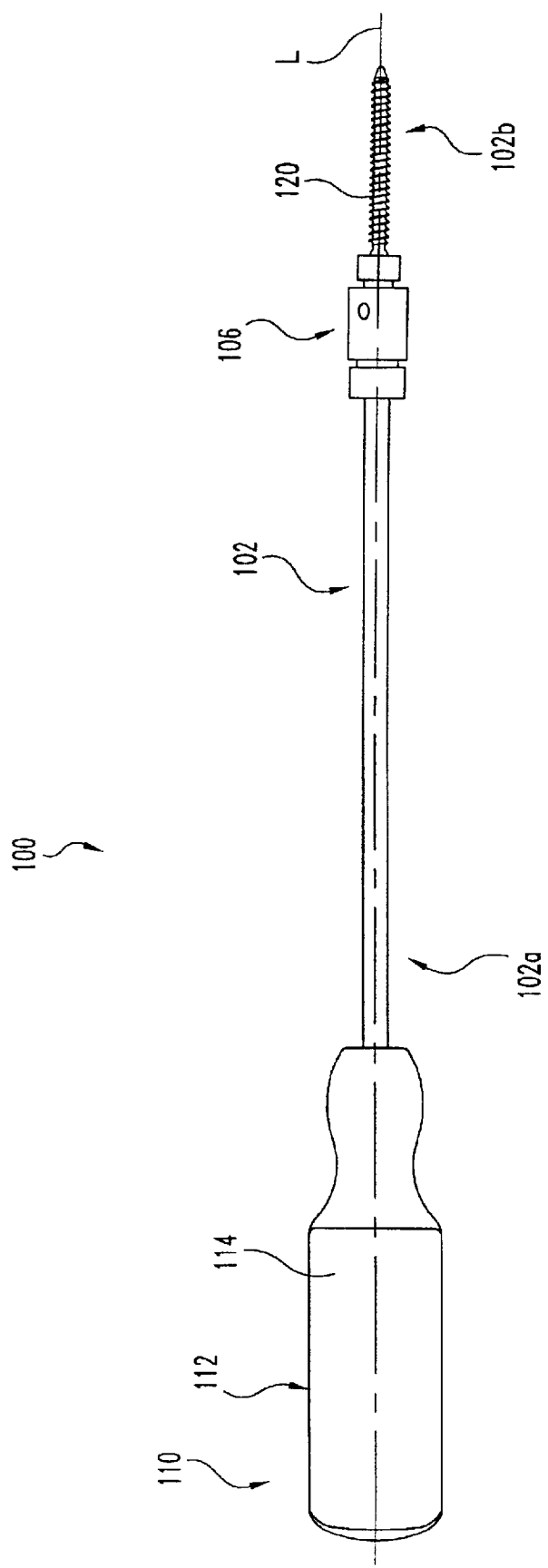
FIG. 5 is a perspective view of a surgical instrument according to another form of the present invention.
Figure 6:
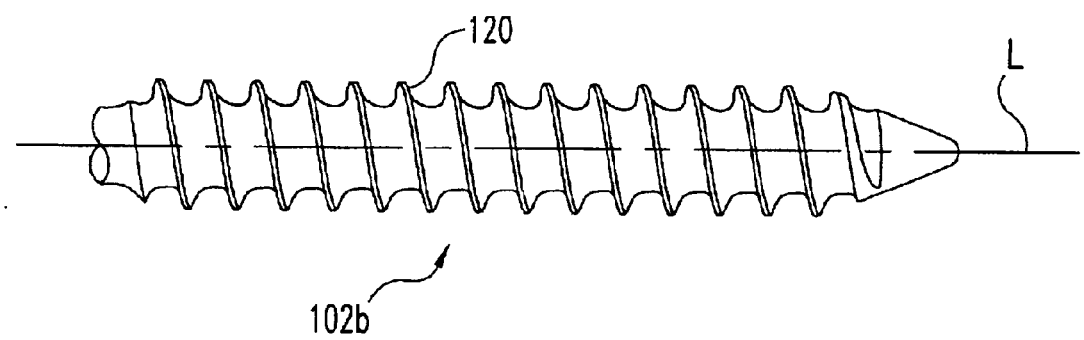
FIG. 6 is a side view of the distal end portion of the surgical instrument illustrated in FIG. 5, as shown in a retracted configuration.

Referring now to FIG. 5, shown therein is a surgical instrument 100 according to another form of the present invention. The surgical instrument 100 is generally comprised of an elongate member 102, a cutting element 104 (FIG. 7), and an actuator mechanism 106. As will become apparent below, the elongate member 102 is preferably configured to form threads along a portion of an axial passage in a skeletal member. As will also become apparent, the cutting element 104 is transitionable between a retracted configuration and an expanded configuration via the selective actuation of actuator mechanism 106. The retracted configuration permits extension of the cutting element 104 through the threaded passage, while the expanded configuration is configured to form an enlarged cross-sectional portion of the axial passage.

The elongate member 102 extends generally along a longitudinal axis L and has a proximal end portion 102a and a distal end portion 102b. Although the elongate member 102 is illustrated as having a generally linear configuration, it should be understood that other configurations are also contemplated, such as, for example, a curvilinear configuration or an angled configuration. Additionally, although the elongate member 102 is illustrated as having a generally circular and substantially uniform outer cross-section, it should be understood that other shapes and configurations are also contemplated as would occur to one of skill in the art. In one embodiment of the invention, a handle 110 is operatively attached to the proximal end portion 102a of elongate member 102. The handle 110 includes a cylindrical-shaped gripping portion 112 defining a gripping surface 114 to aid in the manipulation and positioning of surgical instrument 100 by the surgeon. Although a specific embodiment of the handle 110 has been illustrated and described, it should be understood other types and configurations of handles are also contemplated, such as, for example, a T-handle arrangement or any other suitable handle configuration that would occur to one of skill in the art. It should also be understood that the surgical instrument 100 need not necessarily include a handle, but could alternatively be configured to engage various types of driving tools or possibly a drive motor.

In a preferred embodiment of the invention, a tapping thread 120 is defined along the distal end portion 102b of elongate member 102. The tapping thread 120 is configured to form a threaded axial passage in bone tissue. As should be appreciated, the specific configuration of the tapping thread 120 will be determined by the type of threaded device to be engaged within the threaded axial passage. As will be discussed in further detail below, one such threaded device suitable for use in association with the present invention is a bone screw. However, other types of threaded devices are also contemplated, such as, for example, spinal implants including fusion cages.

Figure 14:
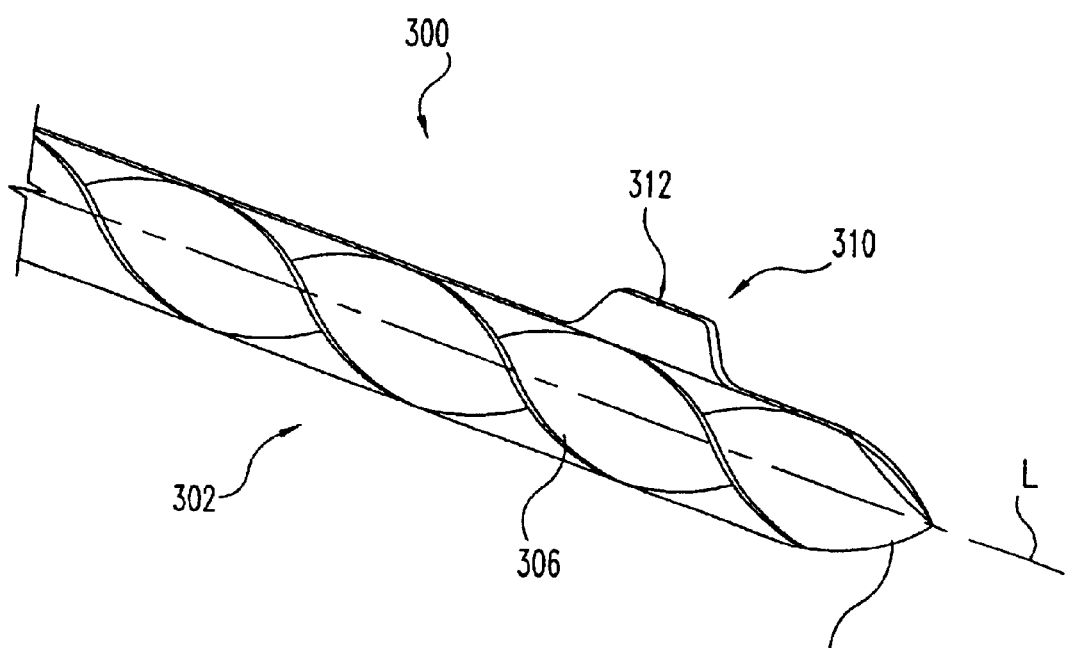
FIG. 14 is a perspective view of the distal end portion of a surgical instrument according to another form of the present invention, as shown in an expanded configuration.

In the illustrated embodiment of the invention, the tapping thread 120 is configured to cut threads along a preformed passage in bone tissue. However, in an alternative embodiment of the invention, the distal end portion 102b of elongate member 102 may be configured to form the axial passage. For example, a self-drilling feature could be incorporated into the design of the distal end portion 102b, such as, for example, by including a cutting flute extending along the distal end portion 102b and/or by including a cutting edge or tip at the distal-most end of end portion 102b. In another embodiment of the invention, the tapping thread 120 could be eliminated and replaced with another type of cutting element suitable for forming an axial passage in bone tissue. For example, referring to FIG. 14, shown therein is a surgical instrument 300 according to another form of the invention. The surgical instrument 300 is configured similar to surgical instrument 100 except for the fact that the distal end portion 302 is shaped like a drill. Specifically, the distal end portion 302 includes a cutting tip 304 and at least one cutting flute 306. The cutting flute 306 may be configured as an axial flute, a helical flute, or any other type of flute that would occur to one of skill in the art.

Referring now to FIGS. 6–11, shown therein is a retracted configuration (FIGS. 6, 8 and 10) and an expanded configuration (FIGS. 7, 9 and 11) of the cutting element 104. The cutting element 104 is generally comprised of a cutting blade portion 130 configured to cut into bone tissue, and a shaft or rod portion 132 configured to operatively coupled the cutting blade portion 130 to the actuator mechanism 106. In one embodiment of the invention, the cutting blade 130 includes a cutting edge 134 having a profile corresponding to the outer profile of the tapping thread 120. The cutting blade 130 preferably defines a pair of thread-like protrusions 136a, 136b that correspond in size and shape to adjacent revolutions of the tapping thread 120. It should be understood, however, that the cutting blade 130 may include any number of protrusions, including a single protrusion or three or more protrusions. It should also be understood that the cutting blade 130 may be configured such that the cutting edge 134 has an outer profile that does not correspond to the outer profile of the tapping thread 120. For example, as shown in FIG. 14, a cutting blade 310 may be provided which includes a cutting edge 312 having an outer profile defining a substantially flat, rectangular configuration. As should be appreciated, other shapes and configurations of cutting blades are also contemplated that would be suitable for forming an enlarged cross-sectional portion of a passage in bone tissue. Furthermore, although the cutting element 104 has been illustrated and described as including a single cutting blade 130, it should be understood that the cutting element 104 could include any number of cutting blades 130 arranged at a single axial location along the elongated member 102 or at multiple axial locations along elongate member 102.

Notably, when the cutting blade 130 is disposed in the retracted configuration, the cutting edge 134 is aligned with the outer profile of adjacent revolutions of the tapping thread 120, but preferably does not extend beyond the outer profile of the tapping thread 120. As will be discussed in further detail below, when disposed in the retracted configuration, the cutting blade 130 will pass through the threaded axial passage formed in the bone tissue by the tapping thread 120 without disrupting or interfering with the formed threads. However, when transitioned to the expanded configuration, the cutting edge 134 of cutting blade 130 will extend beyond the outer profile of adjacent revolutions of the tapping thread 120. As will also be discussed in further detail below, when disposed in the expanded configuration, the cutting blade 130 will cut into bone tissue to form an enlarged cross-sectional portion of the axial passage.

Figure 10:
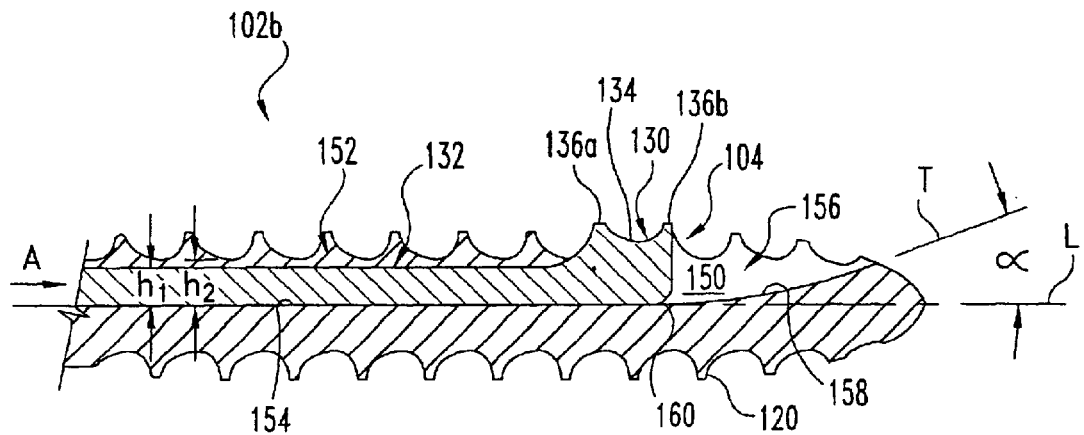
FIG. 10 is a cross-sectional view of the distal end portion of the surgical instrument illustrated in FIG. 6, as shown in the retracted configuration.
Figure 11:
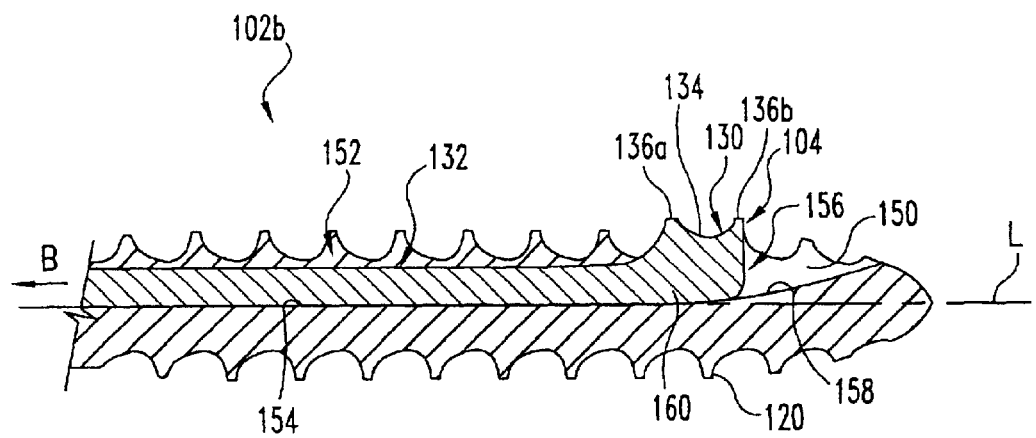
FIG. 11 is a cross-sectional view of the distal end portion of the surgical instrument illustrated in FIG. 7, as shown in the expanded configuration.

In a preferred embodiment of the present invention, the cutting blade 130 is transitioned between the retracted and expanded configurations by axially displacing the cutting blade 130 relative to the elongate member 102. As shown in FIGS. 10 and 11, the elongate member 102 defines an axial channel or passageway 150 extending along the distal end portion 102b. The channel 150 includes an axial section 152 having a substantially flat, non-tapered bottom surface 154 arranged generally parallel with longitudinal axis L, and a ramped or inclined section 156 having an outwardly tapering bottom surface 158 arranged at an acute angle α relative to longitudinal axis L. In one embodiment of the invention, the tapered surface 158 has a curvilinear or arcuate configuration, with a tangent line T of the curve being arranged at an angle α relative to the longitudinal axis L. The angle α preferably falls within a range of 0 degrees to about 45 degrees. However, other angles α are also contemplated as falling within the scope of the present invention, including angles α greater than 45 degrees. Additionally, although the tapered surface 158 has been illustrated and described as having a curvilinear or arcuate configuration, it should be understood that surface 158 may alternatively have an angular configuration, tapering outwardly at a substantially constant angle α.

The cutting element 104 is sized and shaped to be slidably displaced within the axial channel 150. Preferably, the cutting element 104 has a width $w_1$ that is slightly less than the width $w_2$ of the channel 150 to allow the cutting element 104 to be guidably displaced along the axial channel 150 (See FIG. 9). Additionally, the shaft 132 preferably has a height $h_1$ that is slightly less than the height $h_2$ between the bottom surface 154 of channel 150 and the root diameter of the tapping thread 120. As should be appreciated, the height $h_1$ of the shaft 132 is sized to avoid interfering with the tapping operation performed by the tapping thread 120 and to avoid disruption of the threads formed in the bone tissue. Similarly, when disposed in the retracted configuration, the cutting blade 130 defines a cutting profile corresponding to the outer profile of the tapping thread 120 to avoid interfering with the tapping operation and to avoid disruption the threads formed in the bone tissue.

As will be discussed below, the cutting blade 130 is preferably transitioned between the retracted configuration illustrated in FIG. 10 and the expanded configuration illustrated in FIG. 11 in response to a mechanically induced force. Such force may be effected, for example, via the selective actuation of the actuator mechanism 106. The cutting blade 130 is transitioned from the retracted configuration toward the expanded configuration by axially displacing the cutting element 104 along the channel 150 in the direction of arrow A until a lower bearing surface 160 of the cutting blade 130 is engaged against the outwardly tapering surface 158 of the ramped section 156. As the bearing surface 160 is slidably advanced along the tapered surface 158, the cutting blade 130 will correspondingly be urged in an outward or lateral direction toward the expanded configuration illustrated in FIG. 11. Preferably, the bearing surface 160 is rounded or beveled to avoid cutting into the tapered surface 158 as the cutting blade 130 is displaced along channel 150. As should be apparent, the cutting blade 130 may be transitioned back toward the retracted configuration illustrated in FIG. 10 by displacing the cutting element 104 along the channel 150 in the direction of arrow B until the lower bearing surface 160 of the cutting blade 130 disengages the tapered surface 158 of ramped section 156. Although the illustrated embodiment of the invention depicts channel 150 as including the tapered surface 158, it should be understood that the cutting blade 130 could alternatively define a tapered surface configured to interact with a portion of the elongate member 102 to facilitate transitioning of the cutting blade 130 between the retracted and expanded configurations.

Figures 12, 13:
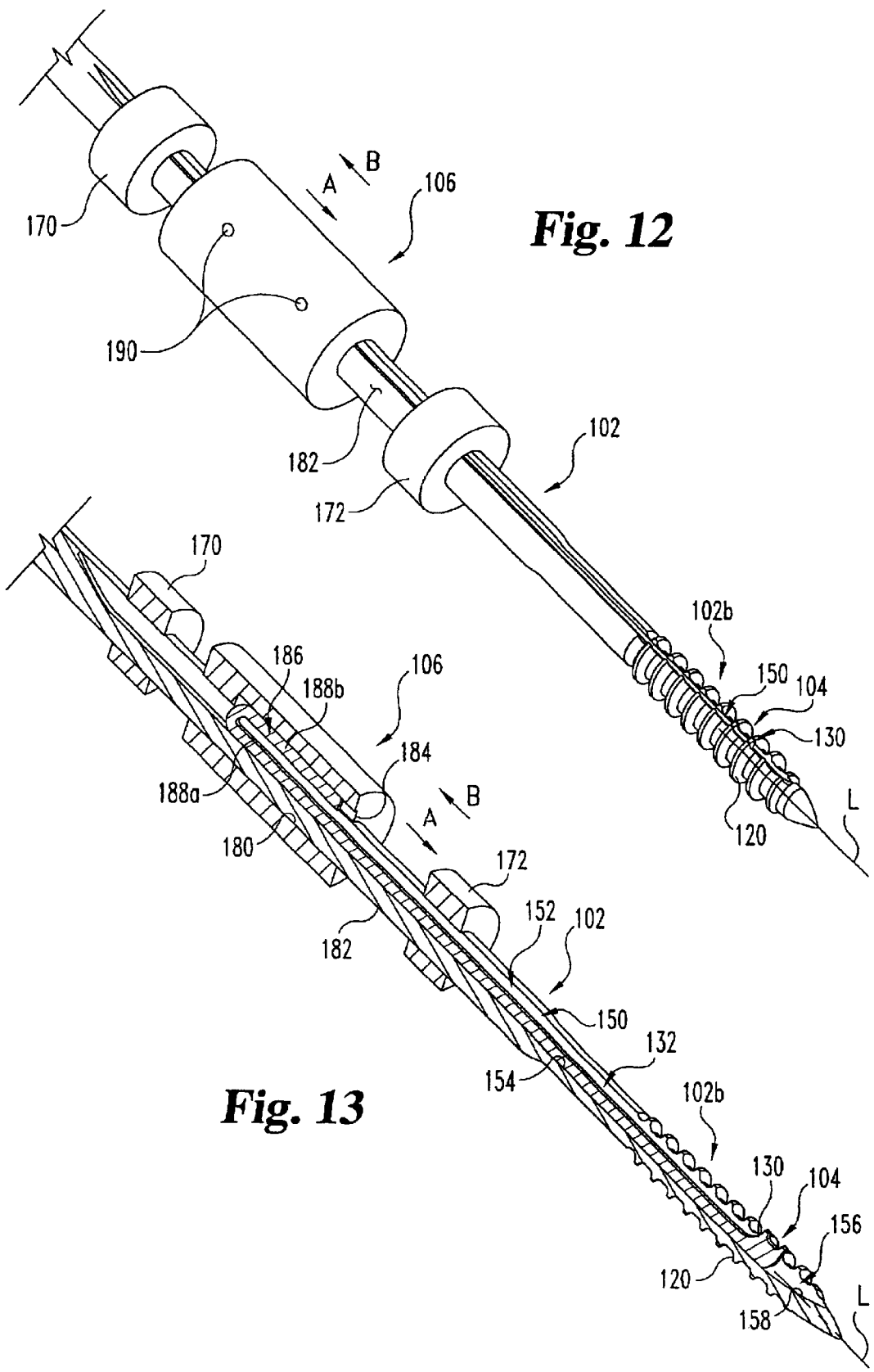
FIG. 12 is a perspective view of one embodiment of an actuator mechanism for use with the surgical instrument illustrated in FIG. 5.
FIG. 13 is a cross-sectional view of the actuator mechanism illustrated in FIG. 12.

Referring to FIGS. 12 and 13, shown therein is an actuator mechanism 106 according to one embodiment of the present invention. The actuator mechanism 106 is coupled to the cutting element 104 and is operable to selectively transition the cutting blade 130 between the retracted and expanded configurations. In the illustrated embodiment, the actuator mechanism 106 is configured as a collet or ring engaged about the elongate member 102 and operatively coupled to the shaft 132 of cutting element 104. As should be appreciated, axial displacement of the collet 106 in the direction of arrow A or arrow B correspondingly displaces the cutting element 104 through the channel 150 and slidably displaces the cutting blade 130 along the ramped section 156 to transition the cutting blade 130 between the retracted and expanded configurations. A pair of stop members 170, 172 are preferably attached to the elongate member 102 and disposed on either side of the collet 106 to limit axial displacement of the collet 106 and corresponding axial displacement of the cutting element 104.

In one embodiment of the present invention, the collet 106 has a cylindrical configuration, defining an inner surface 180 having a diameter slightly larger than the diameter of an outer surface 182 of the elongate member 102. As a result, the collet 106 may be slidably and guidably displaced along the outer surface 180 of the elongate member 102. Although the surfaces 180, 182 have been illustrated and described as having a circular cross section, it should be understood that other cross-sections are also contemplated, such as, for example, square or rectangular cross-sections.

The collet 106 preferably defines a blind keyway 184 generally aligned with the axial portion 152 of channel 150 and having a width approximately equal to the channel width $w_2$. The shaft 132 of cutting element 104 preferably includes a U-shaped portion 186 including a lower leg 188a and an upper leg 188b. The U-shaped portion 186 of shaft 132 is positioned within the keyway 184 and is secured to the collet 106 by way of a number of fasteners 190, such as, for example, a pair of opposing sets of set screws engaging opposite sides of the upper leg 188b. The height of the keyway 184 is preferably sized somewhat less than the height of the U-shaped portion 186 such that the U-shaped portion 186 is resiliently deformed as it is inserted into the keyway 184. As a result, an inward biasing force is established to aid in maintaining the blade portion 130 and the shaft portion 132 in their proper position within channel 150. Notably, the inward biasing force maintains the bottom surfaces of the cutting blade 130 and the shaft 132 in constant engagement against the bottom surface of the channel 150.

Although a specific embodiment of an actuator mechanism 106 has been illustrated and described herein, other embodiments of actuator mechanisms are also contemplated as would occur to one of skill in the art. It should be understood that any type of actuator mechanism configured to transition the cutting element 104 between the retracted and expanded configurations may be used. For example, in an alternative embodiment of the invention, the actuator mechanism 106 may be threadingly engaged with the elongate member 102 and coupled to the cutting element 104 in such a manner as to axially displace the cutting element 104 relative to the elongate member 102 to transition the cutting element between the retracted and expanded configurations. In one such embodiment, the inner surface 180 of collet 106 may be threadingly engaged with the outer surface 182 of the elongate member 102, with the shaft portion 132 of the cutting element 104 being rotatably coupled to the collet 106. As should be appreciated, rotation of the collet 106 would correspondingly axially displace the cutting element 104 relative to the elongate member 102 to transition the cutting blade 130 between the retracted and expanded configurations.

Figure 15:
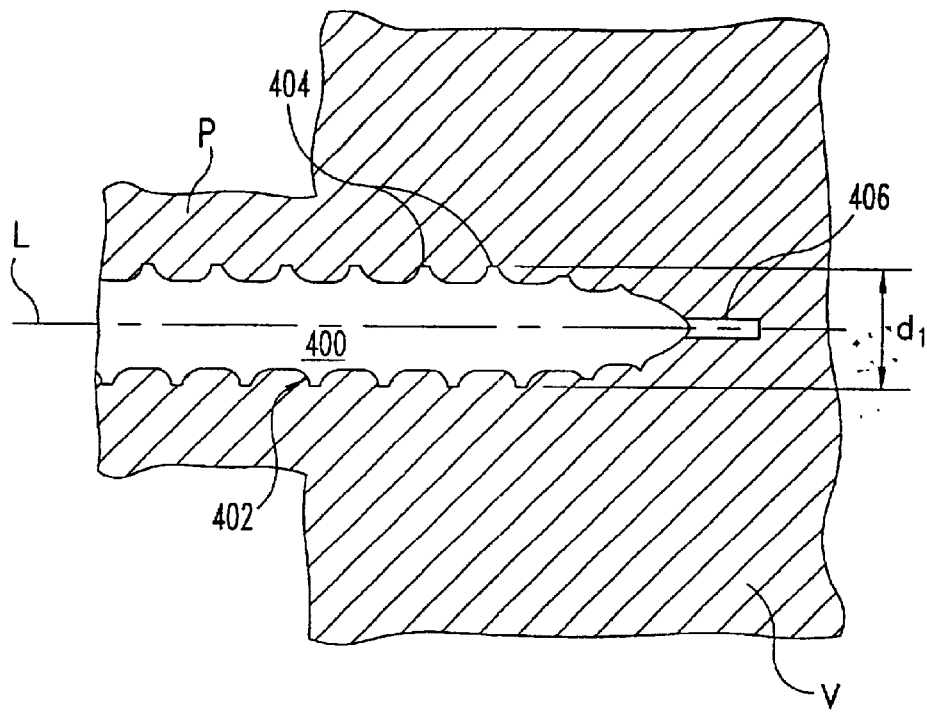
FIG. 15 is a partial cross-sectional side view of a skeletal member, depicting the formation of a threaded portion of an axial passage by the surgical instrument illustrated in FIG. 5.
Figure 16:
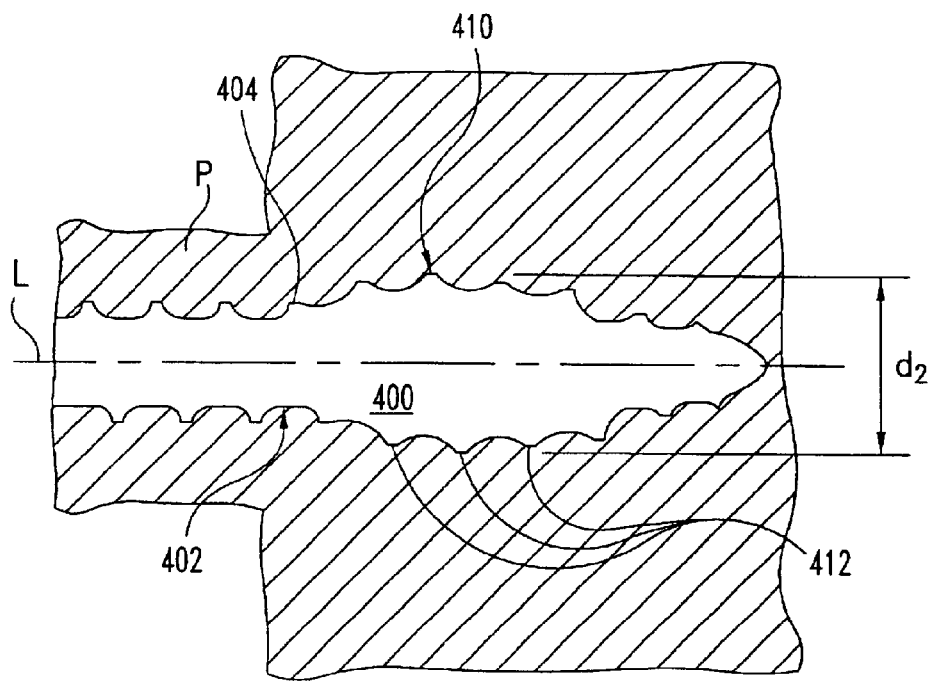
FIG. 16 is a partial cross-sectional side view of the skeletal member illustrated in FIG. 15, depicting the formation of an enlarged cross-sectional of the axial passage by the surgical instrument illustrated in FIG. 5.

Having described various structural features of the surgical instrument 100, a method of using the surgical instrument 100 to form an axial passage in bone having an enlarged cross-section portion will now be discussed in accordance with one form of the present invention. Referring to FIGS. 15 and 16, shown therein is the formation of an axial passage 400 through the pedicle region P of a vertebral body V and into an interior region of the vertebral body V. The axial passage 400 has a threaded portion 402 and an enlarged cross-sectional portion 410, the function of which will be discussed below.

Referring to FIG. 15, with the cutting blade 130 disposed in the retracted configuration (FIG. 6), the distal end portion 102b of the elongate member 102 is engaged with the pedicle P of the vertebral body V and the elongate member 102 is rotated about the longitudinal axis L via application of rotational force to the handle 110. As a result, internal threads 404 having an outer thread diameter $d_1$ are cut into the bone tissue via the tapping thread 120 to form the threaded portion 402 of the axial passage 400 at a predetermined depth. As discussed above, the cutting edge 134 of cutting blade 130 preferably does not extend beyond the outer profile of the tapping thread 120 when in the retracted configuration. As a result, the cutting blade 130 will pass through the threaded portion 402 of axial passage 400 without interfering with the tapping operation and without disrupting or otherwise damaging the internal threads 404.

In one embodiment of the invention, a pilot hole 406 is initially formed in the vertebral body V prior to performing the tapping operation. However, it should be understood that in another embodiment of the invention, the distal end portion 102b of the elongate member 102 may include a self-drilling feature to eliminate the need for a pilot hole 406. As illustrated in FIG. 14, such features may include, for example, the incorporation of a pointed tip and/or a cutting flute into the distal end potion 102b to facilitate penetration and cutting into bone tissue.

Figure 7:
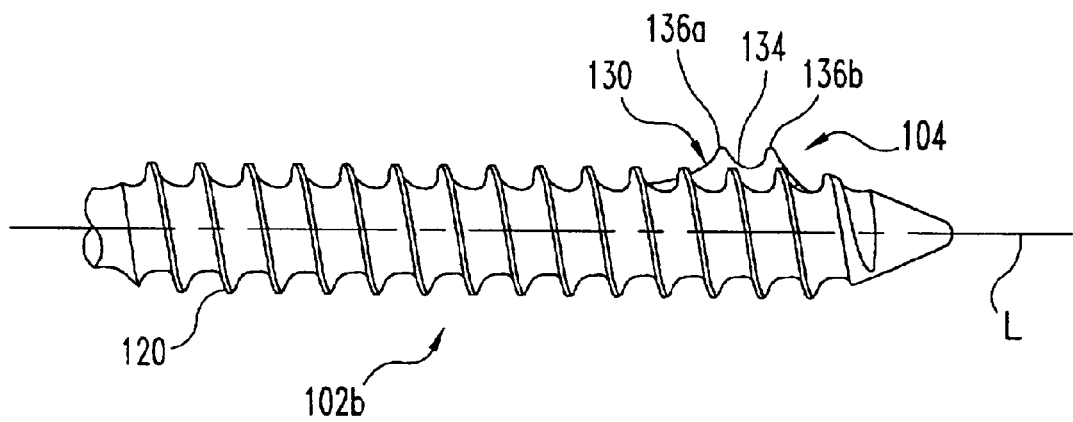
FIG. 7 is a side view of the distal end portion of the surgical instrument illustrated in FIG. 5, as shown in an expanded configuration.
Figure 8:
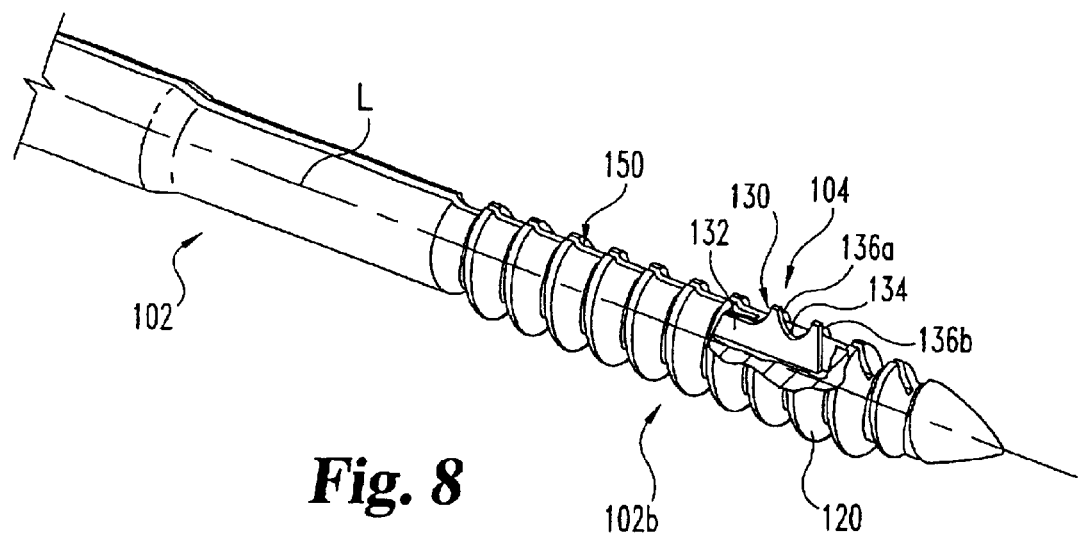
FIG. 8 is a perspective view of the distal end portion of the surgical instrument illustrate d in FIG. 6, as shown in the retracted configuration.
Figure 9:
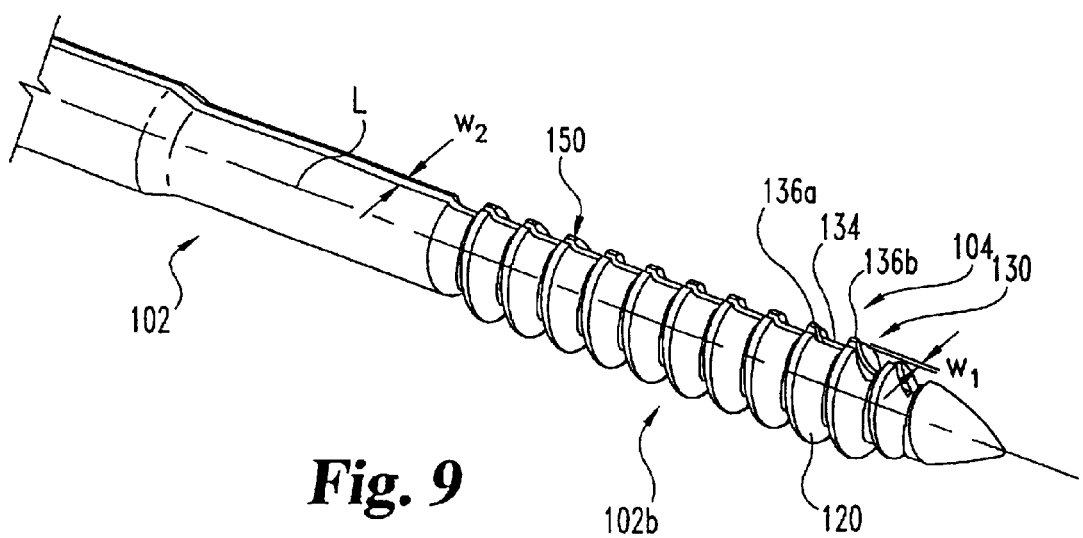
FIG. 9 is a perspective view of the distal end portion of the surgical instrument illustrated in FIG. 7, as shown in the expanded configuration.

Referring to FIG. 16, following formation of the threaded portion 402 of axial passage 400, the cutting blade 130 is transitioned to the expanded configuration (FIG. 7). As discussed above, transitioning between the retracted and expanded configurations is accomplished by axially displacing the cutting blade 130 relative to the elongate member 102, such as might be accomplished, for example, by slidably displacing the collet 106 along the elongate member 102 in the direction of arrow A. The elongate member 102 is then rotated about the longitudinal axis L via application of a rotational force to the handle 110. As a result, the protrusions 136a, 136b of the cutting blade 130 will cut into the adjacent bone tissue to form an enlarged cross-sectional portion 410 of the axial passage 400. As discussed above, the cutting edge 134 of the cutting blade 130 extends beyond the outer profile of the tapping thread 120 when in the expanded configuration to thereby form thread-like grooves 412 having an outer diameter $d_2$ somewhat larger than the outer thread diameter $d_1$ of threads 404.

Following formation of the enlarged cross-sectional portion 410, the cutting blade 130 is transitioned back to the retracted configuration (FIG. 6), such as might be accomplished, for example, by slidably displacing the collet 106 along the elongate member 102 in the direction of arrow B. Notably, since the width $w_1$ of the cutting blade 130 is sized in relatively close tolerance with the width $w_2$ of the axial channel 150 (FIG. 9), the risk of bone or other debris becoming lodged between the cutting blade 130 and the elongate member 120 is substantially reduced, if not eliminated entirely. If such a result were to occur, the cutting blade 130 might be inhibited or restricted from transitioning back to the retracted configuration, thereby preventing removal of the distal portion 102b of elongate member 102 from the axial passage 400.

Following transitioning of the cutting blade 130 back to the retracted configuration, the distal end portion 102b of elongate member 102 may then be removed from the axial passage 400 by unthreading the tapping thread 120 through the threaded portion 402. Since the cutting edge 134 of the cutting blade 130 does not extend beyond the outer profile of the tapping thread 120 when in the retracted configuration, the cutting blade 130 will pass through the threaded portion 402 of axial passage 400 without disrupting or otherwise damaging the internal threads 404 formed therealong.

Figure 17:
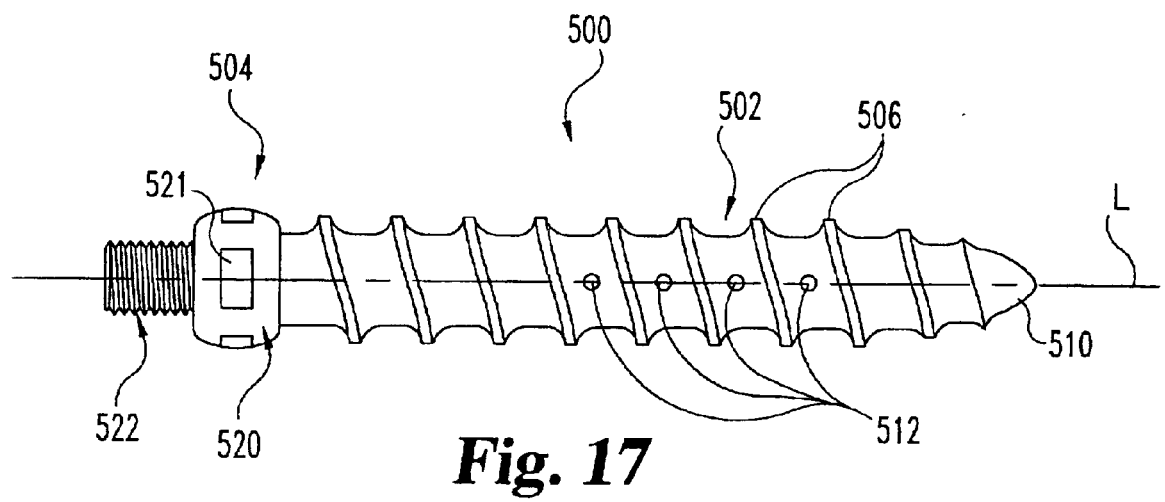
FIG. 17 is a side view of a fenestrated bone screw for use in association with the present invention.
Figure 18:
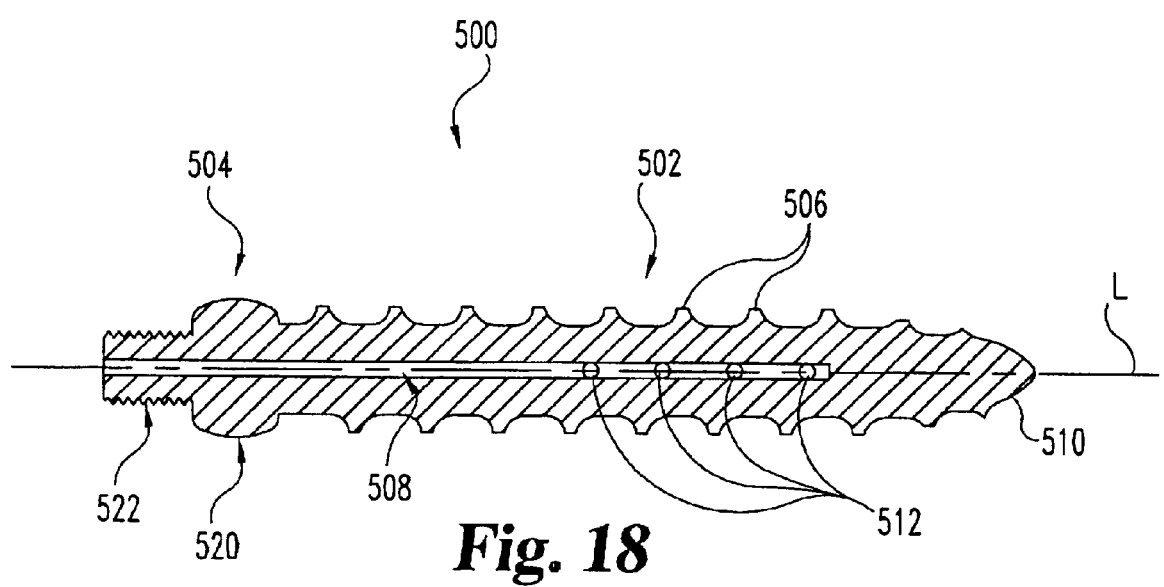
FIG. 18 is a cross-sectional view of the fenestrated bone screw illustrated in FIG. 17.

Referring to FIGS. 17 and 18, shown therein is one embodiment of a bone screw 500 suitable for use with the present invention. The bone screw 500 is configured to threadingly engage the threaded portion 402 of the axial passage 400 formed in the vertebral body V. The bone screw 500 is also configured to deliver an anchoring material into the enlarged cross-sectional portion 410 of the axial passage 400 to secure the bone screw 500 to vertebral body V and to eliminate or at least minimize the likelihood of the bone screw 500 from loosening or cutting away from vertebral body V. In one embodiment of the invention, the anchoring material is bone cement. However, other suitable types of anchoring materials are also contemplated as would occur to one of skill in the art.

The bone screw 500 includes a threaded shank portion 502 and a head portion 504. The threaded shank portion 502 defines a screw thread 506 corresponding to the threads 404 formed along the threaded portion 402 of the axial passage 400. An axial opening 508 extends through the head portion 504 and along a substantial portion of the threaded shank 502. However, the axial opening 508 preferably does not extend entirely through the threaded shank 502 so as to define a closed distal end 510. It should be understood, however, that the axial opening 508 could alternative extend along the entire length of the bone screw 500. A number of fenestration openings 512 extend through the bone screw and are disposed in communication with the axial opening 508. Preferably, the fenestration openings 512 are arranged in four axial grouping along the threaded shank 502, with the openings 512 in each grouping being uniformly positioned about the circumference of the threaded shank 502. In one embodiment, each grouping includes three openings 512 uniformly separated by 120 degrees. The fenestration openings 512 are preferably disposed between adjacent revolutions of the screw thread 506 and are preferably arranged along the distal-half of the threaded shank 502.

The head portion 504 of the bone screw 500 preferably includes a drive portion 520 and a connector portion 522. The drive portion 520 is configured to be engaged by a driving tool (not shown) to facilitate threading insertion of the bone screw 500 in the threaded portion 402 of axial passage 400. In one embodiment, the drive portion 520 is enlarged relative to the connector portion 522 and has a hexagonal shape defining a number of flattened regions 521. However, other configurations of the drive portion 520 are also contemplated as would occur to one of skill in the art. The connector portion 522 is configured to connect to a system for delivering anchoring material to the bone screw 500. The connector portion 522 is also preferably configured to mate with a connector member, such as, for example, a rod or plate, and to accept an anchoring device, such as a nut, to secure the rod or plate to the bone screw 500. In one embodiment, the connector portion 522 comprises a threaded stem extending from the drive portion 520. However, other configurations of the connector portion 522 are also contemplated as would occur to one of skill in the art.

Although a specific embodiment of a bone screw 500 has been illustrated and described herein, it should be understood that other types and configurations of bone screws are also contemplated for use in association with the present invention. For example, another embodiment of a bone screw suitable for use in association with the present invention is described in U.S. patent application Ser. No. 09/746,668 to Chappuis, the contents of which have been incorporated herein by reference. It should also be understood that other types of bone anchors are also contemplated for use in association with the present invention, including both threaded and unthreaded bone anchor devices.

Figure 19:
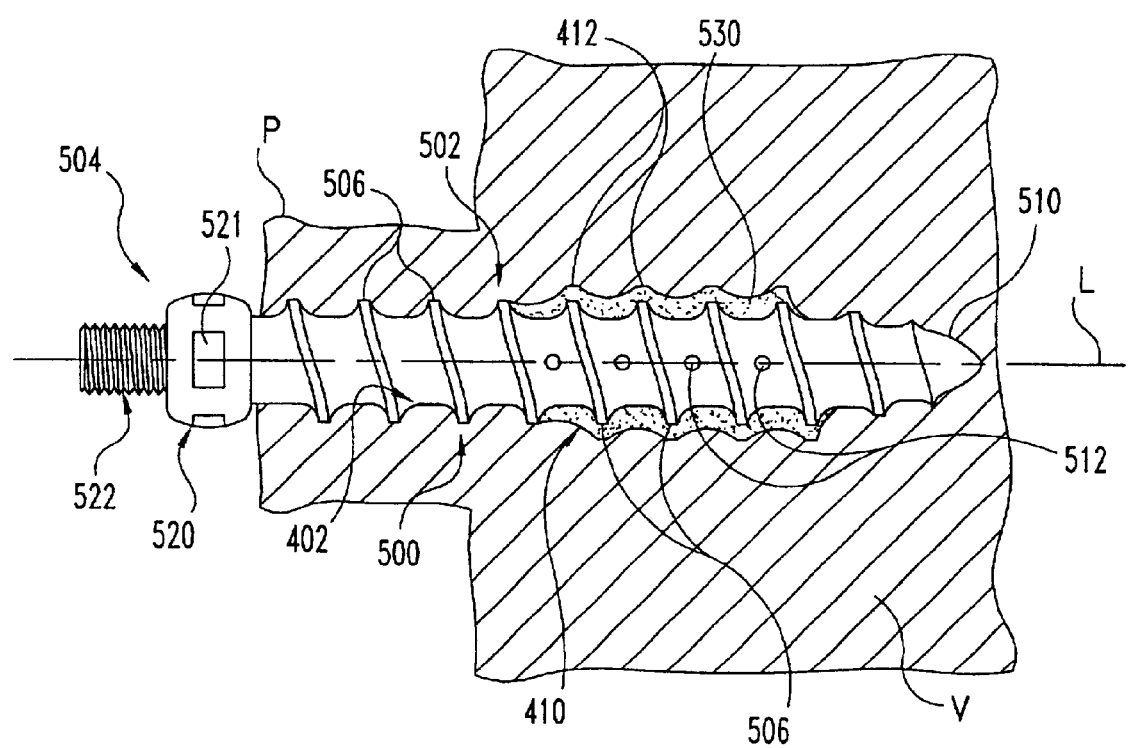
FIG. 19 is a partial cross-sectional side view of the skeletal member illustrated in FIG. 16, depicting insertion of the fenestrated bone screw into the axial passage with the fenestration openings positioned adjacent the enlarged portion of the axial passage.

Referring to FIG. 19, following formation of the axial passage 400 within the vertebral body V and removal of the surgical instrument 100 therefrom, the bone screw 500 is inserted into the axial passage 400. The bone screw 500 is threaded along the threaded portion 402 of axial passage 400 until the fenestration openings 512 are disposed adjacent the enlarged cross-sectional portion 410. Preferably, the threads 506 of the bone screw 500 are disposed adjacent and are generally aligned with the helical grooves 412 of the enlarged cross-sectional portion 410 so as to define a substantially uniform gap or spacing between the threads 506 and the adjacent bone tissue. When the bone screw 500 is properly positioned within the axial passage 400, the head portion 504 is preferably disposed adjacent the outer surface of the vertebral body V.

Following insertion of the bone screw 500 into the axial passage 400, an anchoring material delivery system is attached to the connector portion 522 of head 504. An anchoring material 530, such as, for example, bone cement, is then injected through the axial opening 508, out the fenestration openings 512, and into the enlarged cross-sectional portion 410 of the axial passage 400. One example of a system and method for inserting a bone screw into a vertebral body and for delivering an anchoring material thereto is disclosed in U.S. patent application Ser. No. 09/746,668 to Chappuis, the contents of which have been incorporated herein by reference. However, other suitable systems and methods for inserting a bone screw into a vertebral body and delivering an anchoring material thereto are also contemplated as would occur to one of skill in the art.

As should be appreciated, the enlarged cross-sectional portion 410 of the axial passage 400 facilitates uniform distribution of the bone cement 530 about the threaded shank portion 502 of the bone screw 500 while minimizing disruption to the cancellous bone tissue surrounding the threaded shank 502. Once the bone cement 530 cures or hardens, a cement mantle is formed about the threaded shank 502 to firmly secure the bone screw 500 to the vertebral body V. As should also be appreciated, the cement mantle eliminates or at least minimizes the likelihood of the bone screw 500 from loosening or cutting away from the vertebral body V. As should also be appreciated, formation of the enlarged cross-sectional portion 410 along only a portion of the axial passage 400, while maintaining the threaded portion 402 at a smaller or reduced cross-section, preserves the structural integrity of the vertebral body V. This is particularly advantageous when the bone screw 500 is inserted into the relative delicate pedicle region P of the vertebral body V. In this manner, formation of the axial passage 400 in the vertebral body V and securement of the bone screw 500 within the axial passage 400 by way of a cement mantle is accomplished in a minimally invasive manner.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A surgical instrument, comprising:

an elongate member extending along an axis; and at least one cutting element engaged with said elongate member and being transitionable between a retracted configuration for extending through a first portion of a passage in bone and an expanded configuration for forming a second portion of the passage having an enlarged cross-section; and wherein a portion of said elongate member defines a tapping thread configured to cut threads along the first portion of the passage, and wherein axial displacement of said at least one cutting element relative to said elongate member causes said at least one cutting element to transition between said retracted and expanded configurations to form said second portion of the passage having said enlarged cross-section.

2. The instrument of claim 1, wherein said elongate member and said cutting element define bearing surfaces slidably engaging one another during said axial displacement, at least one of said bearing surfaces including a ramped section configured to transition said cutting element between said retracted and expanded configurations during said axial displacement.

3. The instrument of claim 1, wherein said elongate member defines an axial channel including a ramped section, said at least one cutting element being at least partially disposed within said channel and slidably displaced along said ramped section to transition said cutting element between said retracted and expanded configurations.

4. The instrument of claim 3, further comprising an actuator mechanism engaged with said elongate member and coupled to said at least one cutting element, wherein axial displacement of said actuator mechanism relative to said elongate member slidably displaces said cutting element along said ramped section of said channel to transition said cutting element between said retracted and expanded configurations.

5. The instrument of claim 4, wherein said actuator mechanism comprises a collet slidably engaged about said elongate member wherein axial displacement of said collet relative to said elongate member slidably displaces said cutting element along said ramped section of said channel to transition said cutting element between said retracted and expanded configurations.

6. The instrument of claim 1, wherein said elongate member comprises a sleeve, said at least one cutting element being outwardly biased toward said expanded configuration and being at least partially disposed within said sleeve to selectively maintain said at least one cutting element in said retracted configuration, said at least one cutting element being transitionable between said retracted and expanded configurations by axially displacing said at least one cutting element relative to said sleeve.

7. The instrument of claim 6, further comprising an actuator mechanism including a shaft disposed within said sleeve and coupled to said cutting element, wherein axial displacement of said shaft relative to said sleeve transitions said at least one cutting element between said retracted and expanded configurations.

8. The instrument of claim 6, wherein said at least one cutting element is pivotally coupled to said shaft and is aligned in an axial orientation when in said retracted configuration and in angular orientation when in said expanded configuration.

9. A surgical instrument, comprising:

an elongate member;

a first cutting element disposed along said elongate member for forming a first portion of a passage in bone, said first cutting element comprising a tapping thread; and a second cutting element disposed along said elongate member and being transitionable between a retracted configuration for extending through the first portion of the passage and an expanded configuration for forming a second portion of the passage having an enlarged cross-section.

10. The instrument of claim 11, wherein said first cutting element comprises a drill flute.

11. The instrument of claim 11, wherein said first cutting element comprises a distal end portion of said elongate member.

12. The instrument of claim 9, wherein said second cutting element comprises a cutting blade extending laterally from said elongate member when transitioned toward said expanded configuration.

13. The instrument of claim 12, wherein said elongate member defines a channel extending along an axis with said cutting blade being at least partially disposed within said channel, at least one of said channel and said cutting blade including a ramped section configured to transition said cutting blade between said retracted and expanded configurations when said cutting blade is axially displaced along said channel.

14. The instrument of claim 13, further comprising an actuator mechanism engaged with said elongate member and coupled to said cutting blade, wherein axial displacement of said actuator mechanism relative to said elongate member axially displaces said cutting blade along said channel to transition said cutting blade between said retracted and expanded configurations.

15. A surgical instrument, comprising:

an elongate member;

a first cutting element disposed along said elongate member for forming a first portion of a passage in bone, said first cutting element comprising a distal end portion of said elongate member, said distal end portion of said elongate member configured to be self-drilling and self-tapping; and a second cutting element disposed along said elongate member and being transitionable between a retracted configuration for extending through the first portion of the passage and an expanded configuration for forming a second portion of the passage having an enlarged cross-section.

16. A surgical instrument, comprising:

an elongate member;

a first cutting element disposed along said elongate member for forming a first portion of a passage in bone; and a second cutting element disposed alone said elongate member and being transitionable between a retracted configuration for extending through the first portion of the passage and an expanded configuration for forming a second portion of the passage having an enlarged cross-section; and wherein said first cutting element comprises a tapping thread and wherein said second cutting element comprising a cutting blade.

17. The instrument of claim 16, wherein said cutting blade includes a cutting edge having a profile corresponding to a profile of said tapping thread.

18. A surgical instrument, comprising:

an elongate member;

a tapping thread defined along a portion of said elongate member for forming a threaded portion of a passage in bone; and a cutting blade engaged with said elongate member and being transitionable between a retracted configuration for extending through the threaded portion of the passage and an expanded configuration for forming an enlarged cross-sectional portion of the passage.

19. The instrument of claim 18, wherein said elongate member defines an axial channel including a ramped section, said cutting blade being at least partially disposed within said channel and slidably displaceable along said ramped section to transition said cutting blade between said retracted and expanded configurations.

20. The instrument of claim 19, further comprising a collet engaged with said comprises a collet slidably engaged about said elongate member and coupled to said cutting blade so that axial displacement of said collet relative to said elongate member slidably displaces said cutting blade along said ramped section of said channel to transition said cutting blade between said retracted and expanded configurations.

21. The instrument of claim 18, wherein said cutting blade includes a cutting edge having a profile corresponding to a profile of said tapping thread.

22. A surgical instrument, comprising:

means for tapping threads along a portion of a passage in bone;

means for forming an enlarged cross-sectional portion of the passage; and means for transitioning said means for forming between a retracted configuration for extending through the threaded portion of the passage and an expanded configuration for forming the enlarged cross-sectional portion of the passage.

23. A surgical instrument, comprising:

an elongate member extending along an axis and including:

a tapping portion formed alone a distal portion of said elongate member and configured to cut threads along a passage in bone; and an expandable portion having at least one cutting element transitionable between an axial orientation configured to extend through the axial passage in bone and an angular orientation for enlarging a portion of the axial passage laterally adjacent said threads.

24. The instrument of claim 23, wherein said at least one cutting element is pivotally coupled to said elongate member.

25. The instrument of claim 24, wherein said at least one cutting element is pivotally coupled to a distal end portion of said elongate member.

26. The instrument of claim 23, wherein said at least one cutting element is outwardly biased toward said angular orientation and is initially maintained in said axial orientation by a retention element.

27. The instrument of claim 26, wherein said retention element is a sleeve, said at least one cutting element being at least partially disposed within said sleeve to selectively maintain said at least one cutting element in said axial orientation, said at least one cutting element being transitionable between said retracted and expanded configurations by axially displacing said at least one cutting element relative to said sleeve.

28. The instrument of claim 27, further comprising an actuator mechanism including a shaft disposed within said sleeve and coupled to said at least one cutting element, wherein axial displacement of said shaft relative to said sleeve transitions said at least one cutting element between said axial and angular configurations.

29. The instrument of claim 28, wherein said at least one cutting element is pivotally coupled to said shaft.

30. The instrument of claim 23, wherein the axial passage is formed by applying an axial force to said elongate member; and wherein the axial passage is enlarged by applying a rotational force to said elongate member.

31. The instrument of claim 30, further comprising a handle coupled to said elongate member, said handle configured to transmit said axial and rotational forces to said elongate member.

32. The instrument of claim 23, further comprising a retention element configured to selectively maintain said at least one cutting element in said axial orientation.

33. A surgical instrument, comprising:

an elongate member extending along an axis;

a tapping element formed along a distal portion of said elongate member; and at least one cutting element transitionable between a retracted configuration for extending through a passage in bone and an expanded configuration for enlarging a portion of the passage; and wherein said tapping element is configured to cut threads along the passage, said at least one cutting element configured to enlarge said portion of the passage laterally adjacent said threads when transitioned to said expanded configuration.

34. The instrument of claim 33, wherein said at least one cutting element has a lateral profile corresponding to a lateral profile of said tapping element.

35. The instrument of claim 33, wherein axial displacement of said at least one cutting element relative to said elongate member causes said at least one cutting element to transition between said retracted and expanded configurations.

36. The instrument of claim 35, wherein said elongate member and said cutting element define bearing surfaces slidably engaging one another during said axial displacement, at least one of said bearing surfaces including a ramped section configured to transition said cutting element between said retracted and expanded configurations during said axial displacement.

37. The instrument of claim 33, wherein said elongate member includes another cutting element configured to form the passage in the bone.

38. The instrument of claim 37, wherein said another cutting element comprises a portion of said tapping element.

* * * * *

UNITED STATES PATENT AND TRADEMARK OFFICE
CERTIFICATE OF CORRECTION

PATENT NO.  : 6,814,734 B2
DATED       : November 9, 2004
INVENTOR(S) : Chappuis et al.

It is certified that error appears in the above-identified patent and that said Letters Patent is hereby corrected as shown below:

Column 18,
Lines 49 and 51, replace "claim 11" with -- claim 9 --.

Signed and Sealed this

Nineteenth Day of April, 2005

JON W. DUDAS
*Director of the United States Patent and Trademark Office*